(12) United States Patent
Jeong et al.

(10) Patent No.: US 12,179,013 B2
(45) Date of Patent: Dec. 31, 2024

(54) ELECTRODE DEVICE FOR WRAPPING VESSEL IN THE BODY AND METHOD THEREFOR

(71) Applicant: DEEPQURE INC., Seoul (KR)

(72) Inventors: Chang Wook Jeong, Seoul (KR); Sung Min Park, Seoul (KR); Jin Hwan Baik, Seoul (KR); Dong Hyun Yim, Suwon-si (KR); Du Jin Bach, Seongnam-si (KR)

(73) Assignee: DEEPQURE INC., Seoul (KR)

( * ) Notice: Subject to any disclaimer, the term of this patent is extended or adjusted under 35 U.S.C. 154(b) by 368 days.

(21) Appl. No.: 17/638,921

(22) PCT Filed: Aug. 27, 2020

(86) PCT No.: PCT/KR2020/011484
§ 371 (c)(1),
(2) Date: Feb. 28, 2022

(87) PCT Pub. No.: WO2021/040431
PCT Pub. Date: Mar. 4, 2021

(65) Prior Publication Data
US 2022/0296884 A1    Sep. 22, 2022

(30) Foreign Application Priority Data

Aug. 29, 2019  (KR) .................. 10-2019-0106495
Aug. 27, 2020  (KR) .................. 10-2020-0108605

(51) Int. Cl.
*A61N 1/05*    (2006.01)
*A61B 18/14*   (2006.01)

(52) U.S. Cl.
CPC ............ *A61N 1/0551* (2013.01); *A61B 18/14* (2013.01); *A61B 2018/1407* (2013.01)

(58) Field of Classification Search
CPC .. A61N 1/0556; A61N 1/0551; A61N 1/0558; A61B 2018/142
See application file for complete search history.

(56) References Cited

U.S. PATENT DOCUMENTS

| 9,731,132 B2 | 8/2017 | Deem et al. |
| 2008/0004673 A1 | 1/2008 | Rossing et al. |

(Continued)

FOREIGN PATENT DOCUMENTS

| CN | 103796604 A | 5/2014 |
| CN | 203935269 U | 11/2014 |

(Continued)

OTHER PUBLICATIONS

Euroepan Search Report issued for European Application No. 20858446.6 on Jul. 10, 2023, 7 pages.

(Continued)

*Primary Examiner* — George R Evanisko
(74) *Attorney, Agent, or Firm* — Merchant & Gould P.C.

(57) ABSTRACT

An electrode device for wrapping a vessel in the body according to an embodiment of the present invention comprise an electrode part that surrounds the vessel and denervates or modulates at least some nerves of the vessel; and a guide part that guides movement of the electrode part, wherein the electrode part includes: a first layer that is bent in order for the electrode part to be wound around the vessel; a second layer that is placed on the first layer and is bent in order for the electrode part to be wound in close contact with the vessel; an electrode that is placed on the second layer and denervates or modulates at least some nerves of the vessel with energy from an energy source generator.

16 Claims, 7 Drawing Sheets

(56) References Cited

U.S. PATENT DOCUMENTS

| | | |
|---|---|---|
| 2008/0091275 A1 | 4/2008 | Ducharme |
| 2014/0094887 A1 | 4/2014 | True et al. |
| 2015/0224326 A1* | 8/2015 | Toth .................. A61B 7/04 |
| | | 600/377 |
| 2015/0359589 A1 | 12/2015 | Mauch et al. |
| 2018/0064485 A1 | 3/2018 | Jeong |
| 2019/0133681 A1* | 5/2019 | Jeong ................ A61B 18/1206 |

FOREIGN PATENT DOCUMENTS

| | | |
|---|---|---|
| JP | 2010-506685 A | 3/2010 |
| JP | 2011-152204 A | 8/2011 |
| JP | 2018-020164 A | 2/2018 |
| KR | 10-2003-0035783 A | 5/2003 |
| KR | 10-2017-0058964 A | 5/2017 |
| KR | 10-2019-0097559 A | 8/2019 |
| WO | 2007118090 A2 | 10/2007 |

OTHER PUBLICATIONS

International Search Report issued for International Application No. PCT/KR2020/011484 on Dec. 7, 2020, 6 pages.
Office Action for Chinese Patent Application No. 202080061138.6 (May 29, 2024).

\* cited by examiner

ELECTRODE DEVICE FOR WRAPPING VESSEL IN THE BODY AND METHOD THEREFOR

CROSS-REFERENCE TO RELATED APPLICATIONS

This application is a 35 U.S.C. 371 National Phase Application from PCT/KR2020/011484 filed on Aug. 27, 2020, which claims the benefit of Korean Patent Application No. 10-2019-0106495 filed on Aug. 29, 2019 and Korean Patent Application No. 10-2020-0108605 filed on Aug. 27, 2020 in the Korean Intellectual Property Office, the disclosures of which are incorporated herein by reference in their entirety.

TECHNICAL FIELD

The present disclosure relates to an electrode device for wrapping a vessel in the body and a method thereof.

BACKGROUND

A denervation is a procedure intended to control an abnormally overactive autonomic nervous system by damaging specific nerves. For example, a renal denervation can treat hypertension and heart diseases by damaging renal sympathetic nerves directed to the kidney, and a pulmonary denervation can treat lung diseases by damaging parasympathetic nerves directed to the lung.

Nerves usually enclose the outer walls of vessels, such as blood vessels, bronchial vessels, etc., and it may be necessary to enclose the outer walls of vessels to measure signals from the nerves or transmit electrical impulses or various energies to the nerves to damage or destroy the nerves. However, if an electrode is not in proper contact with a nerve or its surrounding tissue, the efficiency may be impaired. Therefore, since vessels enclosed by respective nerves have different dimeters, electrodes of various sizes are needed to enclose the vessels. For example, when a procedure is performed on the renal artery, the main renal artery has a diameter of from 5 mm to 7 mm and varies in size from person to person and has different sizes depending on the location. Also, some people may have various anatomical variations in vessels, such as branched renal artery and accessory renal artery, and the diameters thereof may be from 1 mm to 2 mm. Also, when a denervation is performed on the lung, the diameters of the bronchial vessels increase to a maximum of 300 mm to 400 mm during inhalation and decrease to a minimum of 160 mm to 200 mm during exhalation.

Therefore, it is necessary to change and apply an electrode suitable for size of treatment site every time, and even with an electrode of almost equivalent size, the treatment effect may be remarkably different depending on the degree of completion of contact.

DISCLOSURE OF THE INVENTION

Problems to be Solved by the Invention

Accordingly, there has been a need for a method to effectively enclose vessels of various diameters with one electrode.

Means for Solving the Problems

As a technical means for achieving the above-described technical problem, an electrode device for wrapping a vessel in the body according to an embodiment of the present invention comprise an electrode part that surrounds the vessel and denervates or modulates at least some nerves of the vessel; and a guide part that guides movement of the electrode part, wherein the electrode part includes: a first layer that is bent in order for the electrode part to be wound around the vessel; a second layer that is placed on the first layer and is bent in order for the electrode part to be wound in close contact with the vessel; an electrode that is placed on the second layer and denervates or modulates at least some nerves of the vessel with energy from an energy source generator.

Further, a method for wrapping a vessel according to another embodiment of the present invention comprises a process in which the first layer is bent in order for the electrode part to be wound around the vessel; a process in which the second layer is bent in order for the electrode part to be wound in close contact with the vessel; and a process in which the electrode denervates or modulates at least some nerves of the vessel with energy from an energy source generator.

The above-described the means for solving the problems do not describe all the feature of the present invention. Various features of the present invention and its advantages and effects may be understood in more detail with reference to the following specific embodiments.

Effects of the Invention

According to an embodiment of the present disclosure, it is possible to enclose vessels of various diameters with nerves in the human body, flexibly apply only one electrode to the vessels of various diameters without changing to another electrode suitable for each size and effectively achieve various medical purposes, such as measuring signals from nerves, stimulating nerves, damaging or destroying nerves, etc., as intended by effectively bringing the electrode into contact with the nerves.

BEST MODE FOR CARRYING OUT THE INVENTION

Hereafter, embodiments will be described in detail with reference to the accompanying drawings so that the present disclosure may be readily implemented by a person with ordinary skill in the art. Detailed descriptions of functions or configurations known in the art may be omitted to avoid obscuring the subject matter of the present disclosure. Further, throughout the drawings, the same reference numerals will refer to the same or like parts.

Further, through the whole document, the term "connected to" or "coupled to" that is used to designate a connection or coupling of one element to another element includes both a case that an element is "directly connected or coupled to" another element and a case that an element is "electronically connected or coupled to" another element via still another element. Furthermore, the term "comprises or includes" and/or "comprising or including" used in the document means that one or more other components, steps, operation and/or existence or addition of elements are not excluded in addition to the described components, steps, operation and/or elements unless context dictates otherwise.

The present application is based on US Patent Publication No. US2018/0064485, which was previously filed by the present inventors and the contents of which may be incorporated in the embodiments of the present disclosure described below.

Figure 1:
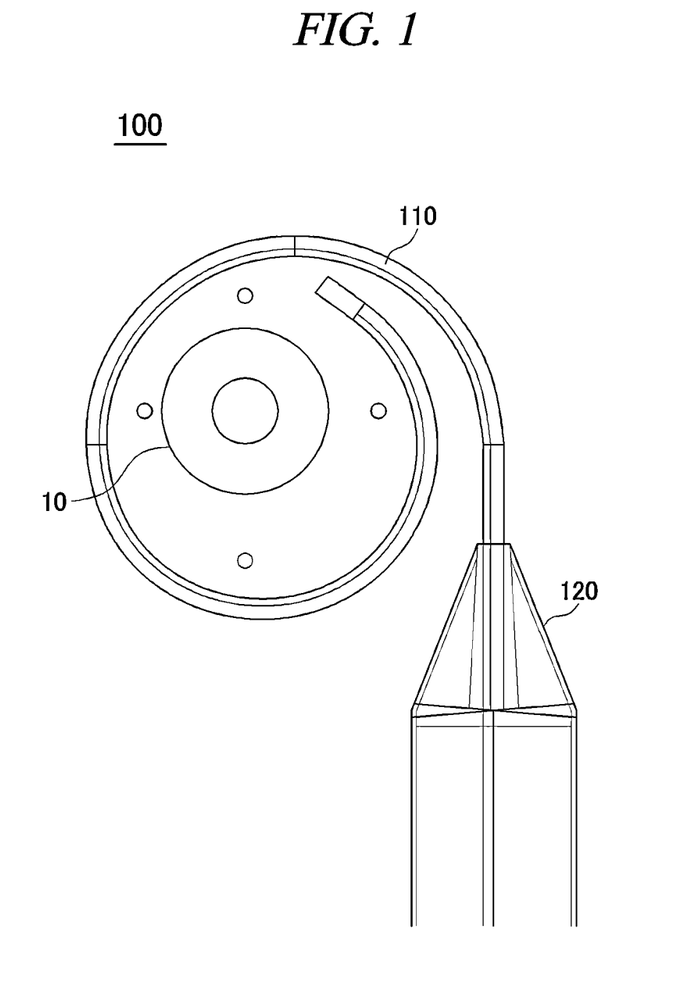
FIG. 1 is a schematic diagram of an electrode device according to an embodiment of the present disclosure.

FIG. 1 is a schematic diagram of an electrode device according to an embodiment of the present disclosure.

Referring to FIG. 1, an electrode device 100 according to an embodiment of the present disclosure may include an electrode part 110 and a guide part 120. The electrode device 100 is configured to enclose vessels 10 of various diameters in the human body.

In the present disclosure, the term "vessel" refers to not only blood vessels, but also various vessels, such as hepatic artery, spleen artery and pulmonary artery, and nerves thereof.

The electrode device 100 may further include an in-body imaging device, such as an endoscope, which provides an image of a target vessel enclosed by the electrode device 100. For example, the in-body imaging device enables an operator to check a site to be damaged or destroyed and monitor a procedure in real time.

The electrode part 110 is configured to enclose the outer wall of a vessel with nerves in the human body, and can be wound by itself when it comes out from the guide part 120.

The electrode part 110 may have a structure in which a first layer, a second layer and an electrode are stacked from below. The electrode part 110 has a width of from 3 mm to 5 mm and a thickness of from 0.1 T to 0.2 T.

Here, the first layer may have a circular shape so as to enclose the outer wall of a vessel when the electrode part 110 is located near the outer wall of the vessel. However, the first layer does not have to be a layered structure that forms a circle shape with a single structure, but may have any structure, such as a plurality of link structures, wrapping the outer wall of a vessel.

The second layer may be configured to adjust the diameter of the electrode to be the same as the diameter of a vessel in order for the electrode to be wound in close contact with the vessel. The method of brining the electrode into close contact with the vessel through the first layer and the second layer will be described in detail with reference to FIG. 3 to FIG. 7.

The second layer is made of, for example, an insulating material that does not conduct electricity, and may be made of an elastic material or a non-elastic material capable of withstanding temperatures equal to or greater than a predetermined temperature (about 40° C.).

Further, the electrode is configured for denervation or modulation by wrapping the outer wall of a vessel, and may be made of a material, such as stainless steel or gold, which is harmless to the human body and conducts electricity well. The electrode may also measure a signal from a nerve of the vessel.

The electrodes may transmit various types of energy from non-illustrated energy source generators. Energies transmitted by the electrode may include, for example, radio-frequency (RF) energy, electrical energy, laser energy, ultrasonic energy, high-intensity focused ultrasound energy, cryogenic energy and other thermal energies.

Here, the energies have a temperature of, for example, from 50° C. to 60° C. or higher, which is a second transformation temperature of the first layer.

According to an embodiment, the electrode may be implemented as an FPCB (Flexible PCB) for transmitting RF energy, a transducer for transmitting ultrasonic energy or a metal electrode for transmitting high-voltage energy and thus may transmit energy to damage nerves.

The electrode part 110 may be further equipped with various sensors necessary for controlling the operation of the electrode part 110.

The guide part 120 is configured to guide movement of the above-described electrode part 110. According to an embodiment, as shown in FIG. 1, one end of the electrode part 110 may be inserted into the guide part 120 to allow only forward and backward movement of the electrode part 110 and suppress lateral movement of the electrode part 110, i.e., to guide the electrode part 110 to show only linear movement.

Figure 2:
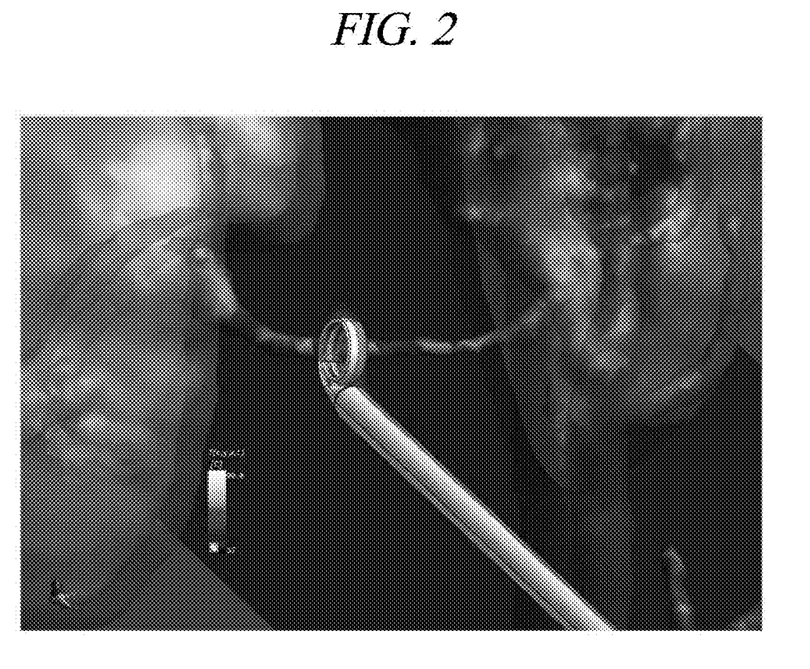
FIG. 2 is a diagram showing an example in which a renal artery is enclosed using an electrode device according to an embodiment of the present disclosure.

FIG. 2 is a diagram showing an example in which a renal artery is enclosed using an electrode device according to an embodiment of the present disclosure.

FIG. 2 shows an example in which the kidney is represented in green color and the artery of a human body is represented in red color and the renal artery coming from the aorta is enclosed using an electrode device according to an embodiment of the present disclosure.

Figure 3A:
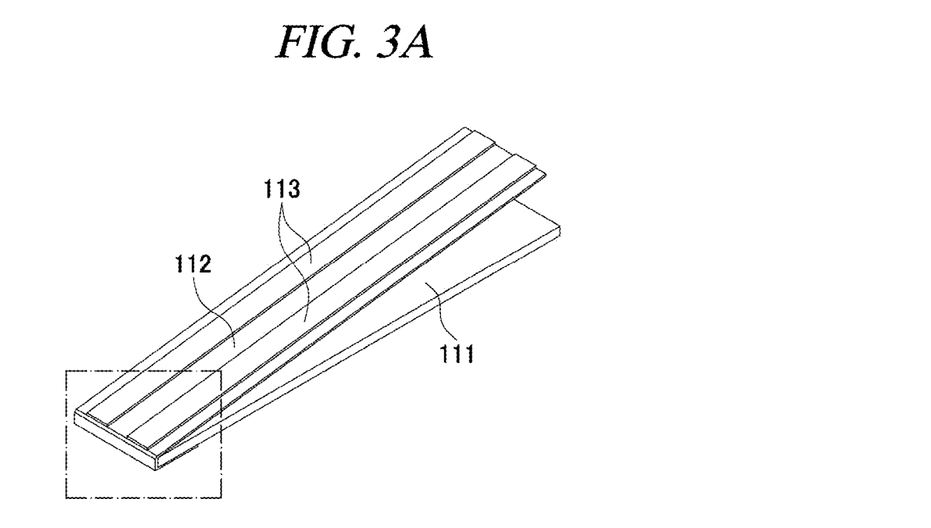
FIGS. 3A and 3B are diagrams illustrating a detailed configuration of an electrode part according to an embodiment of the present disclosure.
Figure 3B:
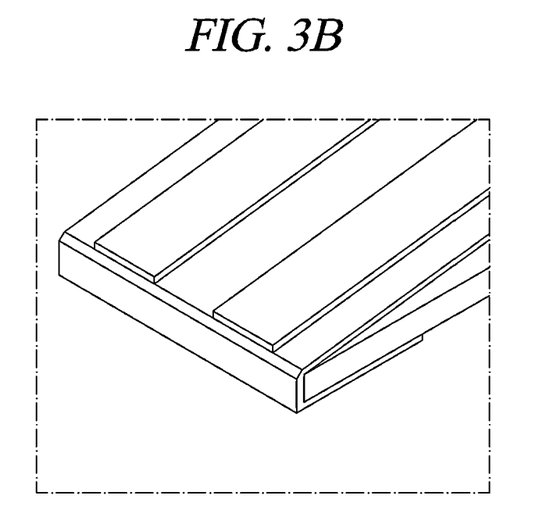

FIG. 3 is a diagram illustrating a detailed configuration of an electrode part according to an embodiment of the present disclosure.

As shown in FIG. 3A, the electrode part has a structure in which a first layer 111, a second layer 112 and an electrode 113 are stacked sequentially from below, and when the electrode part 110 encloses a vessel, the first layer 111 is located on the outer side and the electrode 113 is put in close contact with the outer wall of the vessel.

At least a portion of the first layer 111 may be made of a unidirectional shape memory alloy, a bidirectional shape memory alloy or a spring heat-treated elastic body. For example, at least a portion of the first layer 111 may be made of Nitinol containing at least one of nickel (Ni), titanium (Ti), chromium (Cr), copper (Cu), iron (Fe), lead (Pb), carbon (C), cobalt (Co), hydrogen ($H_2$) and oxygen ($O_2$).

The term "shape memory alloy" refers to an alloy that can be deformed but returns to its pre-deformed shape when heated to a specific temperature or higher.

At high temperature, the shape memory alloy is in a cubic austenite phase, but at low temperature, the shape memory alloy undergoes phase transformation to an orthorhombic martensite phase. This transformation from austenite to martensite when cooled from high temperature is called martensite transformation.

Martensitic transformation starts at a martensite transformation start temperature Ms and ends at a martensite transformation finish temperature Mf. When an external force is applied to the shape memory alloy in the martensite phase, the shape memory alloy, unlike other metals, undergoes transformation without changes in relative locations among atoms.

However, when the shape memory alloy in the martensite phase is heated to an austenite transformation start temperature As, the shape memory alloy returns to its original shape at an austenite transformation finish temperature Af.

The bidirectional shape memory alloy returns to its original shape when heated and also returns to the martensite phase when cooled, and remembers both its high-temperature shape and its low-temperature shape.

According to an embodiment of the present disclosure, the shape memory alloy, which is at least a portion of the first layer 111, may be bent with a first curvature at a first transformation temperature (austenite transformation start temperature) or higher and bent with a second curvature at a second transformation temperature (austenite transformation finish temperature) or higher. Here, the first transformation temperature may range from 35° C. to 40° C. corresponding to body temperature and the second transformation temperature may range from 50° C. to 60° C.

Here, the first curvature may be greater than the diameter of the vessel and the second curvature may be substantially similar to the diameter of the vessel. That is, the first curvature is greater than the second curvature.

Also, the shape memory alloy, which is at least a portion of the first layer 111, may be unbent straight at a third transformation temperature (martensite transformation start temperature) or lower. Here, the third transformation temperature may range from 20° C. to 25° C. That is, the electrode part is kept straight inside the guide part.

In this configuration, when the electrode part 110 comes out of the guide part and is inserted near the renal artery, the first layer 111 is heated to the first transformation temperature by body temperature, and, thus, the electrode part 110 is wound with the first curvature by the first layer 111. Here, the electrode part 110 does not completely enclose the vessel.

Then, as will be described below, when energy from the electrode is transmitted to the first layer 111, the first layer 111 is heated to the second transformation temperature, and, thus, the electrode part 110 is wound with the second curvature by the first layer 111. That is, the second transformation temperature of the first layer 111 is reached by energy from the electrode. Here, the electrode part 110 may completely enclose the vessel depending on the diameter of the vessel. That is, if the vessel has a small diameter, the electrode part 110 may completely enclose the vessel, but if the vessel has a large diameter, the electrode part 110 may not completely enclose the vessel.

When a procedure on the vessel is completed, energy from the electrode is not transmitted to the first layer 111 and the temperature of the first layer 111 is decreased to the first transformation temperature. Accordingly, the electrode part 110 is transformed from the second curvature to the first curvature by the first layer 111 and the operator can safely remove the electrode part 110 from the vessel.

When all the procedures are completed, the electrode part 110 is removed from the body and the temperature of the first layer 111 is decreased to the third transformation temperature. Accordingly, the electrode part 110 is unbent straight by the first layer 111.

As shown in FIG. 3A and FIG. 3B, the first layer 111 and the second layer 112 are fixed and connected only at their one ends and adjacent surfaces thereof are not attached to each other, and the electrode 113 may be attached to an upper surface of the second layer 112.

According to an embodiment of the present disclosure, the electrode part 110 may pull the second layer 112 toward the guide part while the vessel is enclosed by the first layer 111 in order to adjust the electrode 113 to the diameter of the vessel or regulate a contact force between them. Here, when the second layer 112 is pulled toward the guide part, the diameter of the second layer 112 is adjusted so as to correspond to the diameter of the vessel.

The electrode 113 may be attached to the upper surface of the second layer 112. The electrode 113 may include two electrodes 113 arranged in parallel and spaced apart at a predetermined distance to form a bipolar configuration. Each electrode 113 has a width of from 0.5 mm to 1 mm and a thickness of from 0.01 T to 0.1 T. The distance between the electrodes 113 may be from 1.5 mm to 2 mm.

By arranging the electrodes 113 in parallel to each other, it is possible to localize a current path between the electrodes 113, and, thus, nerves of the vessel can be completely removed without damaging the organs adjacent to the vessel.

That is, by localizing heat between the electrodes 113, it is possible to effectively and safely remove the nerves of the vessel.

Although not shown in FIG. 3, a temperature sensor may be provided between the electrodes 113 on the second layer 112. Alternatively, a temperature sensor may be placed at a location corresponding to a space between the electrodes 113 on the first layer 111.

As described above, heat is distributed between the electrodes 113, and by placing the temperature sensor at a location corresponding to the space between the electrodes 113, it is possible to accurately measure the temperature around the electrodes.

Figure 4A:
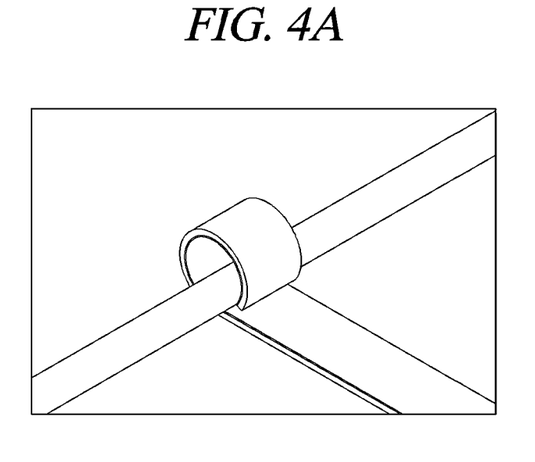
FIGS. 4A and 4B are diagrams provided to explain a method of operating the electrode part according to an embodiment of the present disclosure.
Figure 4B:
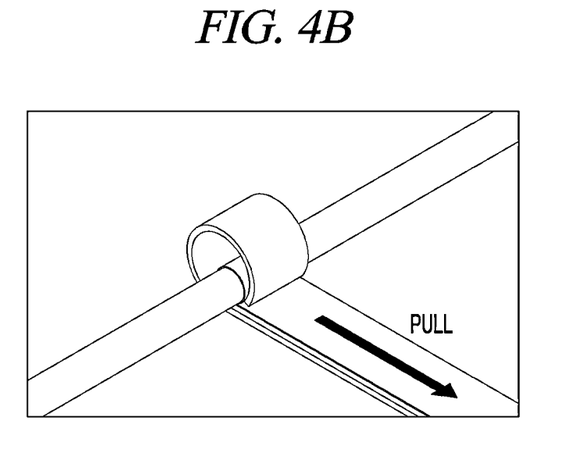

FIG. 4 is a diagram provided to explain a method of operating an electrode part according to an embodiment of the present disclosure.

First, as shown in FIG. 4A, when the electrode part is inserted near the renal artery and energy from the electrode is transmitted to the first layer, the temperature of the first layer increases to the first transformation temperature and reaches the second transformation temperature, and, thus, the first layer is wound with the second curvature around the outer wall of the vessel.

Thereafter, as shown in of FIG. 4B, when the second layer is pulled backwards, the first layer does not move and is kept in a circular shape, and since the first layer and the second layer are fixed and connected at their one ends, the diameter of the second layer is decreased. Accordingly, the electrode attached to the upper surface of the second layer may be adjusted to the diameter of the vessel so as to be in close contact with the outer wall of the vessel.

Figure 5:
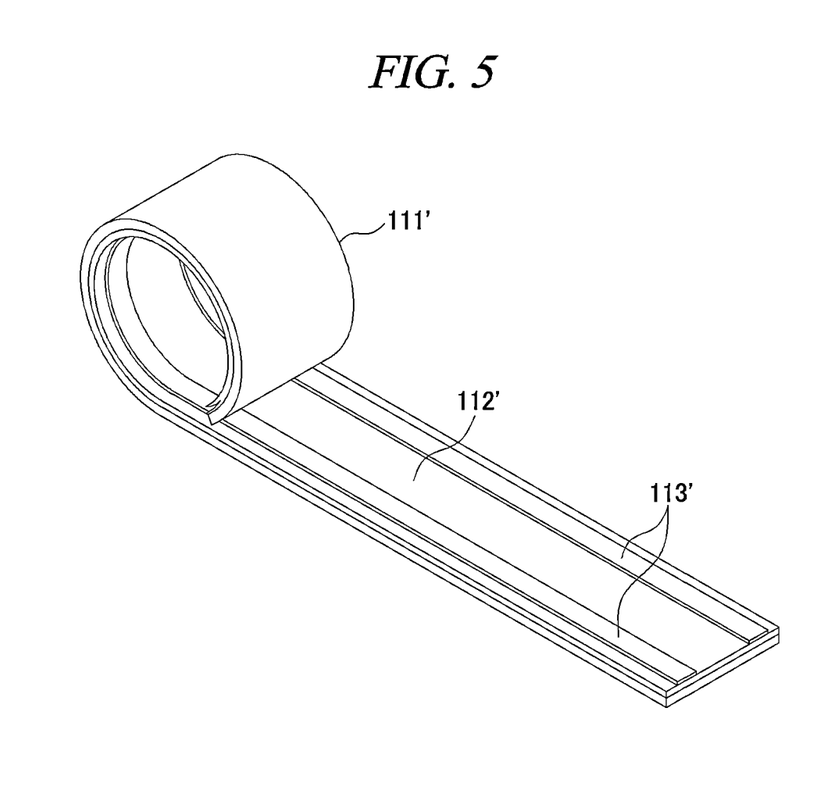
FIG. 5 is a diagram illustrating a detailed configuration of an electrode part according to another embodiment of the present disclosure.

FIG. 5 is a diagram illustrating a detailed configuration of an electrode part according to another embodiment of the present disclosure.

As shown in FIG. 5, the electrode part has a structure in which a first layer 111', a second layer 112' and an electrode 113' are stacked sequentially from below, and when the electrode part 110 encloses a vessel, the first layer 111' is located on the outer side and the electrode 113' is put in close contact with the outer wall of the vessel. Although not shown in FIG. 5, various sensors may be provided at any point on the second layer 112' or on the electrode 113'.

Also, the second layer 112' forms an inner space through which a gas or fluid can flow, and its one surface adjacent to the first layer 111' is fixed and attached to the first layer 111' and the other surface opposite to the adjacent surface is not fixed. Further, the electrode 113' may be attached to the other surface of the second layer 112'.

While the electrode part 110 according to the second embodiment of the present disclosure illustrated in FIG. 5 encloses the vessel, the volume of the second layer 112' may be changed by using a gas or fluid to adjust the electrode 113' to the diameter of the vessel. To this end, the second layer 112' may be made of a material that is more flexible and stretches well. Here, when the volume of the second layer 112' is changed, the diameter of the second layer 112' is adjusted so as to correspond to the diameter of the vessel.

Figure 6A:
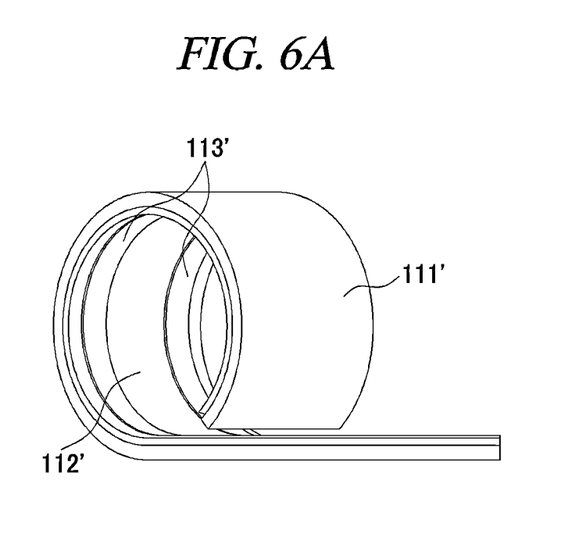
FIGS. 6A and 6B and FIGS. 7A and 7B are diagrams provided to explain a method of operating the electrode part according to another embodiment of the present disclosure.
Figure 6B:
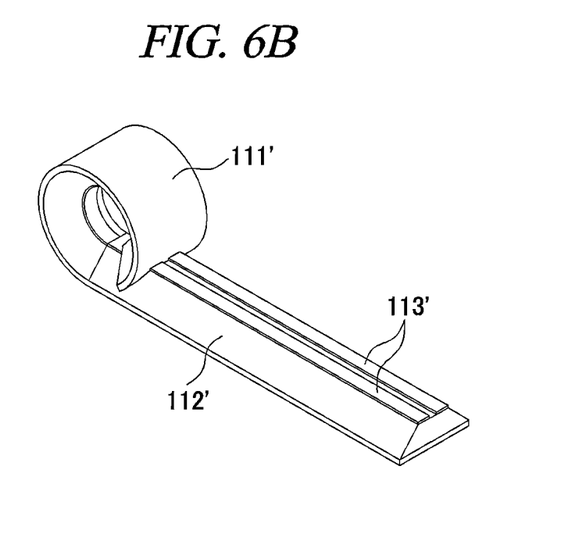
Figure 7A:
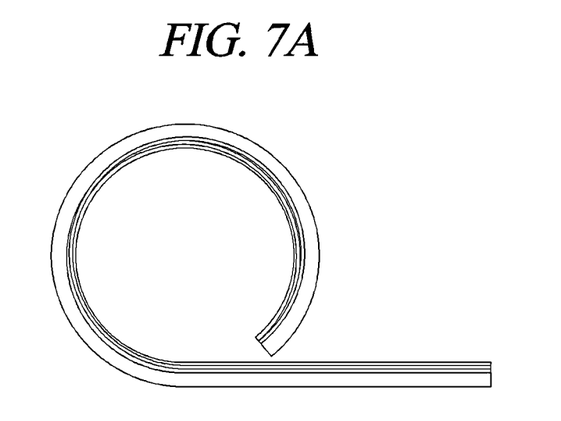
Figure 7B:
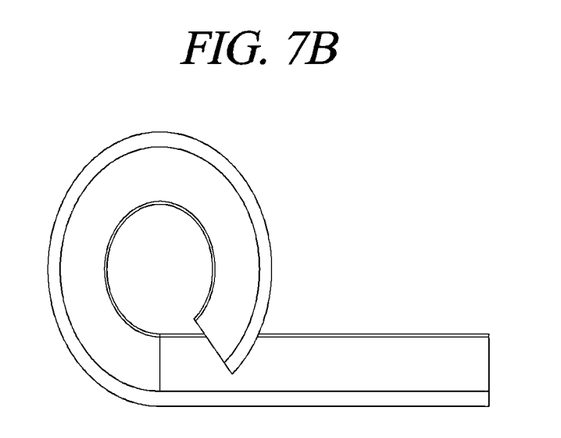

FIG. 6 and FIG. 7 are diagrams provided to explain a method of operating the electrode part according to another embodiment of the present disclosure, and FIG. 6 is a perspective view and FIG. 7 is a side view.

First, as shown in FIG. 6A and FIG. 7A, the first layer 111' is formed into a circular shape to enclose the outer wall of the vessel. Then, as shown in FIG. 6B and FIG. 7B, when the volume of the second layer 112' is increased by filling the inner space of the second layer 112' with a gas or fluid, the diameter of the other surface of the second layer 112' is decreased. Accordingly, the electrode 113' attached to the other surface of the second layer 112' may be adjusted to the diameter of the vessel so as to be in close contact with the outer wall of the vessel.

Figure 8:
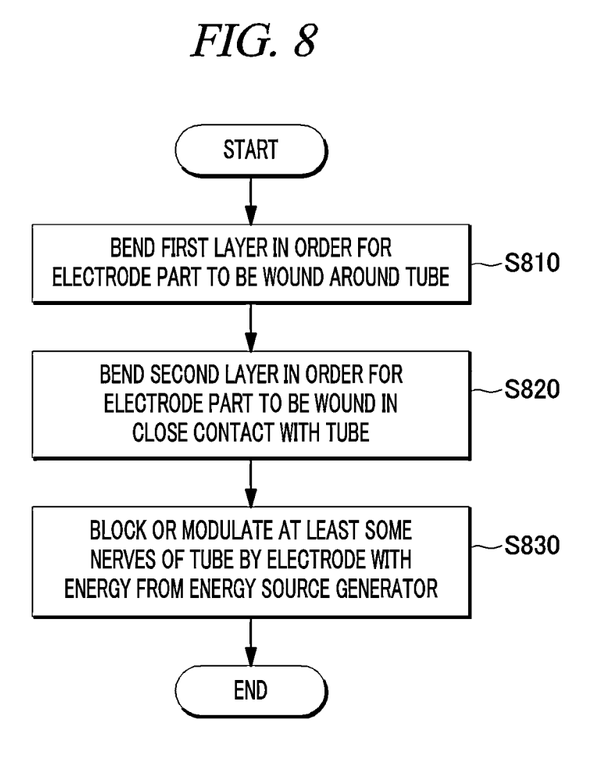
FIG. 8 is a flowchart showing a method of wrapping a vessel according to another embodiment of the present disclosure.

FIG. 8 is a flowchart showing a method of wrapping a vessel according to another embodiment of the present disclosure.

Referring to FIG. 8, in a process S810, the first layer may be bent in order for the electrode part to be wound around the vessel.

In a process S820, the second layer may be bent in order for the electrode part to be wound in close contact with the vessel.

In a process S830, the electrode may denervate at least some nerves of the vessel with energy from an energy source generator.

The electrode according to the embodiments of the present disclosure described above can be used not only for denervation, but also as an electrode wrapping nerves to measure nerve signals.

The present disclosure is not limited to the above-described embodiments and the accompanying drawings. It will be appreciated by a person with ordinary skill in the art that substitutions, modifications and variations of the components according to the present disclosure may be made without departing from the scope of the present disclosure.

We claim:

1. An electrode device for wrapping a vessel in a body, comprising:
    an electrode part configured to surround the vessel and configured to denervate or modulate at least some nerves of the vessel; and
    a guide part that guides movement of the electrode part, wherein the electrode part includes:
    a first layer configured to be bent such that the electrode part is wound around the vessel;
    a second layer that is placed on the first layer and configured to be bent such that the electrode part is wound in close contact with the vessel;
    an electrode placed on the second layer and configured to perform the denervation or modulation of the at least some nerves of the vessel using energy received from an energy source generator,
    wherein at least a portion of the first layer is made of a shape memory alloy, and the shape memory alloy is bent with a first curvature at a first transformation temperature or higher and bent with a second curvature at a second transformation temperature or higher.

2. The electrode device of claim 1,
    wherein the first layer is configured to be heated to the first transformation temperature by body temperature.

3. The electrode device of claim 1,
    wherein the first layer is configured to be heated to the second transformation temperature by the energy received from the energy source generator.

4. The electrode device of claim 1,
    wherein the second curvature is smaller than the first curvature.

5. The electrode device of claim 1,
    wherein the first transformation temperature ranges from 35° C. to 40° C. and the second transformation temperature ranges from 50° C. to 60° C.

6. The electrode device of claim 1,
    wherein the shape memory alloy is a bidirectional shape memory alloy.

7. The electrode device of claim 6,
    wherein the bidirectional shape memory alloy is unbent straight at a third transformation temperature or lower.

8. The electrode device of claim 7,
    wherein the third transformation temperature ranges from 20° C. to 25° C.

9. The electrode device of claim 1,
    wherein the second layer forms an inner space through which a gas or fluid flows, and one surface of the second layer adjacent to the first layer is fixed and attached to the first layer and another surface of the second layer, opposite to the one surface, is not fixed to the first layer.

10. The electrode device of claim 9,
    wherein the electrode device is configured such that after the first layer surrounds the vessel, a volume of the second layer is changed to adjust a diameter of the second layer so as to correspond to a diameter of the vessel.

11. An electrode device for wrapping a vessel in a body, comprising:
    an electrode part configured to surround the vessel and configured to denervate or modulate at least some nerves of the vessel; and
    a guide part that guides movement of the electrode part, wherein the electrode part includes:
    a first layer configured to be bent such that the electrode part is wound around the vessel;
    a second layer that is placed on the first layer and configured to be bent such that the electrode part is wound in close contact with the vessel;
    an electrode placed on the second layer and configured to perform the denervation or modulation of the at least some nerves of the vessel using energy received from an energy source generator,
    wherein the first layer and the second layer are fixed and connected only at one respective end of each, and adjacent surfaces thereof are not attached to each other.

12. The electrode device of claim 11,
    wherein the electrode device is configured such that after the first layer surrounds the vessel, the second layer is pulled toward the guide part to adjust a diameter of the second layer so as to correspond to a diameter of the vessel.

13. A method of wrapping a vessel in a body by using an electrode device including: an electrode part that includes a first layer, a second layer and an electrode arranged sequentially, the electrode part configured to surround the vessel and configured to denervate or modulate at least some nerves of the vessel; and a guide part configured to guide movement of the electrode part, the method comprising:

bending the first layer such that the electrode part is wound around the vessel;

bending the second layer such that the electrode part to be is wound in close contact with the vessel; and denervating or modulating the at least some nerves of the vessel with the electrode, using energy received from an energy source generator, wherein at least a portion of the first layer is made of a shape memory alloy, and the shape memory alloy is bent with a first curvature at a first transformation temperature or higher and bent with a second curvature at a second transformation temperature or higher.

14. The method of claim 5, wherein the bending of the first layer such that the electrode part is wound around the vessel includes:

heating the first layer to the first transformation temperature by body temperature; and heating the first layer to the second transformation temperature by the energy received from the energy source generator.

15. The method of claim 13, wherein the bending of the second layer is such that the electrode part is wound in close contact with the vessel includes:

pulling the second layer toward the guide part to adjust a diameter of the second layer so as to correspond to a diameter of the vessel.

16. The method of claim 13, wherein the bending of the second layer such that the electrode part is wound in close contact with the vessel includes:

a process in which a volume of the second layer is changed to adjust a diameter of the second layer so as to correspond to a diameter of the vessel.

* * * * *